United States Patent
Grez et al.

(10) Patent No.: US 10,149,969 B2
(45) Date of Patent: Dec. 11, 2018

(54) SKIN TREATMENT APPLIANCE WITH CHANGEABLE WORKPIECE

(71) Applicants: Joseph Grez, North Bend, WA (US); Zane Miller, Seattle, WA (US); Scott Straka, Kirkland, WA (US); James Christopher McInnes, Seattle, WA (US)

(72) Inventors: Joseph Grez, North Bend, WA (US); Zane Miller, Seattle, WA (US); Scott Straka, Kirkland, WA (US); James Christopher McInnes, Seattle, WA (US)

(73) Assignee: L'Oréal, Paris (FR)

( * ) Notice: Subject to any disclaimer, the term of this patent is extended or adjusted under 35 U.S.C. 154(b) by 105 days.

(21) Appl. No.: 14/496,891

(22) Filed: Sep. 25, 2014

(65) Prior Publication Data
US 2016/0089525 A1  Mar. 31, 2016

(51) Int. Cl.
*A61M 35/00* (2006.01)
*A61B 17/54* (2006.01)
*A61M 37/00* (2006.01)
*A61B 90/90* (2016.01)
*A61B 17/00* (2006.01)
(Continued)

(52) U.S. Cl.
CPC ........... *A61M 35/003* (2013.01); *A61B 17/54* (2013.01); *A61B 90/90* (2016.02); *A61M 37/00* (2013.01); *A61B 90/96* (2016.02); *A61B 90/98* (2016.02); *A61B 2017/00398* (2013.01); *A61B 2017/00473* (2013.01); *A61B 2017/00734* (2013.01); *A61B 2017/00747* (2013.01); *A61M 2037/0007* (2013.01); *A61M 2205/50* (2013.01); *A61M 2205/6018* (2013.01);
(Continued)

(58) Field of Classification Search
CPC ................ A61M 35/003; A61M 37/00; A61M 2210/04; A61M 2037/0007; A61M 2205/50; A61M 2205/6018; A61M 2205/6027; A61M 2205/6054; A61B 17/54; A61B 2017/00398; A61B 2017/00473; A61B 2017/00734; A61B 2017/00747
See application file for complete search history.

(56) References Cited

U.S. PATENT DOCUMENTS

2002/0049463 A1* 4/2002 Friedman ....... A61B 17/320068
606/169
2002/0188183 A1* 12/2002 Kusakabe ................ A61B 5/00
600/300
(Continued)

*Primary Examiner* — Gary Jackson
*Assistant Examiner* — Zahed Kabir
(74) *Attorney, Agent, or Firm* — Clark A. Puntigam; Jensen & Puntigam, P.S.

(57) ABSTRACT

The appliance includes an appliance body/handle and an interface assembly for receiving a detachable workpiece. The body/handle includes a signal-generating assembly with electrical connections to the appliance body interface. The signal-generating assembly is controlled by a microprocessor, which generates signals adapted to control and operate the workpiece which is attached to the appliance. A plurality of workpieces are included which are individually adapted for treating various spot skin irregularities. The appliance further includes a system for identifying the workpiece attached, so that appropriate operating signals can be generated and provided to the attached workpiece.

11 Claims, 7 Drawing Sheets

(51) Int. Cl.
  *A61B 90/96*    (2016.01)
  *A61B 90/98*    (2016.01)

(52) U.S. Cl.
  CPC .............. *A61M 2205/6027* (2013.01); *A61M 2205/6054* (2013.01); *A61M 2210/04* (2013.01)

(56) References Cited

U.S. PATENT DOCUMENTS

| | | | | |
|---|---|---|---|---|
| 2005/0080359 A1* | 4/2005 | Zhao | ........................ | A61N 7/02 601/2 |
| 2006/0122631 A1* | 6/2006 | Kertz | ..................... | A61B 17/54 606/131 |
| 2007/0293918 A1* | 12/2007 | Thompson | ......... | A61N 1/36021 607/72 |
| 2008/0200861 A1* | 8/2008 | Shalev | ..................... | A61Q 9/04 604/20 |
| 2008/0209650 A1* | 9/2008 | Brewer | ............... | A46B 15/0002 15/22.1 |
| 2009/0318852 A1* | 12/2009 | Reed | .................... | A61M 35/003 604/22 |
| 2010/0121419 A1* | 5/2010 | Douglas | ............... | A61N 5/0616 607/90 |
| 2012/0291777 A1* | 11/2012 | Gordon | ................ | A61M 11/005 128/200.16 |
| 2012/0316457 A1* | 12/2012 | Meng | ................... | A61B 5/0532 600/548 |
| 2013/0046212 A1* | 2/2013 | Nichols | .................... | A46B 7/04 601/18 |
| 2015/0305969 A1* | 10/2015 | Giraud | ................... | A61H 7/005 601/18 |
| 2016/0081878 A1* | 3/2016 | Marks | ................... | A61J 1/2096 604/414 |
| 2017/0273768 A1* | 9/2017 | Bax | ........................ | A61C 17/34 |

\* cited by examiner

| Test | Sensed impedance range | Tip type |
|---|---|---|
| AC resistance frequency sweep or noise generator | Open circuit one direction, > 0.4 Ohm other direction. | LED |
| | 0-1 ohm | Thermoelectric element |
| | 2-4 Ohm | Heating element |
| | Variable 10 ohm to 10k ohm | Iontophoresis tip |
| | Open circuittill 20Khz, then 50 ohm or less between 20Khz to 10 MHz | Ultrasound transducer |
| | Open circuit to 2 GHz | Radio Frequency |
| | Open circuit beyond 2 GHz | None installed. |

FIG. 8

| Tip type | Some examples of appropriate Electrical signal for each tip type |
|---|---|
| LED | Regulated DC current. PWM, flash rate etc. as needed. For example properly poled DC 150 mA, or AC 150mA RMS. |
| Thermoelectric element | Battery voltage switched to produce correct time-averaged voltage, for example poled 10 volts at 50% duty cycle top provide the equivalent of 5 volts time-averaged. |
| Heating element | Battery voltage switched to produce correct time-averaged voltage in response to thermistor or thermocouple feedback. Or a PTC heating element can self-regulate in which case only a CD voltage is required. For example a variably modulated 3 volts in response to the temperature feedback value, or a constant 3 volts with current variable based on the temperature-based resistance of the heating element. |
| Iontophoresis tip | Constant current, for example, 100 mA |
| Ultrasound transducer | AC signal matching resonance of UL transducer in head, from 20kHz to 10 MHz, for example a LRC circuit whereas the piezoelectric element provides the capacitance and is free-running at the piezo resonance. |
| Radio Frequency | AC signal matching impedance of antenna in head from 10 MHz into the GHz range. |

FIG. 9

SKIN TREATMENT APPLIANCE WITH CHANGEABLE WORKPIECE

TECHNICAL FIELD

This invention relates generally to skin treatment appliances, and more specifically concerns such an appliance which is adapted for treatment of small area spots and local skin irregularities.

BACKGROUND OF THE INVENTION

Skin treatment appliances which are used for generalized treatment of skin are well known. One example, among others, is shown in U.S. Pat. No. 7,320,691, owned by the assignee of the present invention. However, many skin conditions occur as spots, i.e. localized irregularities within a specific area, generally less than a few centimeters in diameter. In many such cases, it is unnecessary to treat larger skin areas, when attempting to provide treatment to small area irregularities. Further, an individual may have several spots, each of which require a different form of treatment. As examples, these spots or irregularities may include surface blemishes, age spots, specific skin discolorations, clogged pores, acne, various wounds, insect bites, rashes, rosacea, ingrown hairs, warts, tattoos and other irregularities. Each of these conditions can be best treated with its own regimen and may require a specific device and/or a specific formulation with an active ingredient. Each of these treatments typically requires a workpiece with an active element designed specifically for treatment, including activation of a specific formulation. It is not efficient or reasonable to expect a consumer to purchase separate devices for numerous different specific skin conditions. Accordingly, it would be desirable for a single appliance to be adaptable to treat a wide variety of spot skin irregularities.

SUMMARY OF THE INVENTION

Accordingly, the skin treatment appliance with changeable workpieces, comprising: and appliance body; an appliance body interface assembly for receiving workpieces; a signal generator with electrical connections to the appliance body interface, wherein the signal generator, controlled by a microprocessor, generates signals which are adapted to control and operate the workpiece attached thereto; at least two workpieces, each workpiece adapted to treat a selected spot skin irregularity; and a system for identifying the workpiece attached to the appliance body interface, wherein each of the workpieces has an interface assembly for mechanically and electrically connecting to the appliance body interface.

BRIEF DESCRIPTION OF THE DRAWINGS

FIG. 8 is a table showing a specific signal arrangement for determining the type of workpiece attached to the appliance body.

FIG. 9 is a table showing a number of workpieces and the associated operating signal necessary to operate them.

BEST MODE FOR CARRYING OUT THE INVENTION

Figure 1:
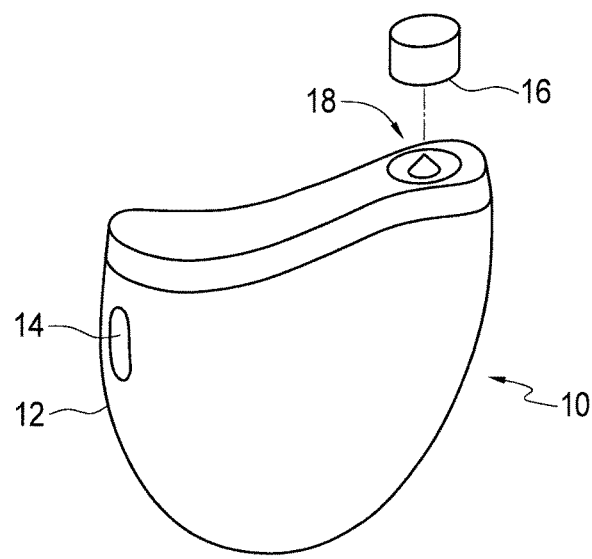
FIG. 1 shows a prior art skin formulation applicator.

A presently known skin formulation dispenser 10 is shown in FIG. 1. The dispenser includes a body 12, an on/off switch 14 and a detachable soft workpiece 16 which is adapted to carry a skin formulation and fits onto a mounting member 18 in the body. The appliance includes a motor (not shown) which moves the workpiece back and forth, toward and away from the skin of a user at a selected frequency. The appliance is useful for the specific task of infusion of skin formulations, usually in the facial area. However, it is not particularly useful in treating particular spot conditions, each of which may require a specific type of treatment method in addition to a specific formulation.

Figure 2:
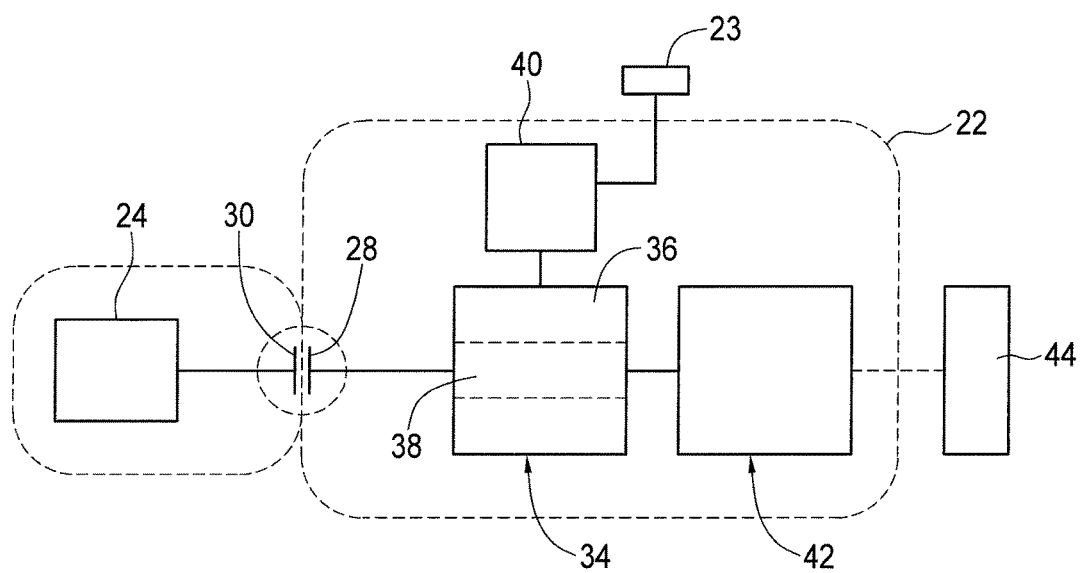
FIG. 2 is a simplified block diagram of the appliance of the present invention.

The present invention is adapted to treat a variety of skin spot irregularities with changeable workpieces and a signal-generating assembly for producing the signals to operate the various workpieces. This is shown very generally in FIG. 2, in which an appliance body is shown at 22, which can be similar to body/handle 12 of FIG. 1. The appliance includes an on/off switch 23. One changeable workpiece is shown generally at 24, for illustration, which is attachable/detachable from appliance body/handle 12. Each workpiece includes a specific active element which is designed to treat a specific spot skin condition, described in more detail with various examples below. The operation of the appliance requires an electrical connection between the appliance body and the workpiece, with the appliance body including a handle interface assembly 28 and the workpiece including a workpiece interface assembly 30. The appliance body includes a signal assembly 34 which can include a sensing module 36 and a signal generator 38 controlled by a microprocessor 40. The microprocessor and the signal assembly draw power from a power supply or battery, shown generally at 42. The battery can be rechargeable, with a separate charging member 44.

The workpiece 24 is a selected one of a variety of different workpieces, each of which is arranged and adapted for treatment of a particular skin condition. Examples of various workpieces include an LED, a thermoelectric element, a heating element, an iontophoresis tip, an ultrasound transducer and a radio frequency workpiece, among others. These are only examples of workpieces which have specific outputs for treatment of particular localized skin irregularities. Typically, a localized irregularity will be a spot or the like with an area of a few centimeters. One characteristic of the workpiece action is a direct effect on the skin irregularity, but another characteristic is increased infusion of a selected active formulation at the desired location, leading to improved condition of the skin irregularity. Additional possibilities include stimulation of tissue or other biological effect to promote healing or regeneration of the particular irregularity.

Figure 5A:
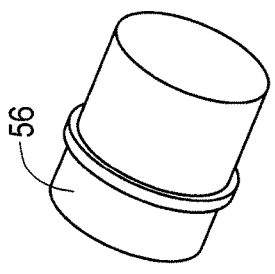
FIGS. 5A and 5B are perspective views of one treatment workpiece and the workpiece mounted in an appliance body.
Figure 6A:
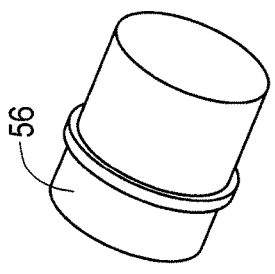
FIGS. 6A and 6B are perspective views of a second treatment workpiece and the workpiece mounted in an appliance body.
Figure 7A:
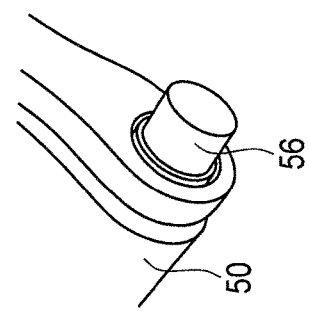
FIGS. 7A and 7B are perspective views of another workpiece and it's the workpiece mounted in an appliance body.
Figure 5B:
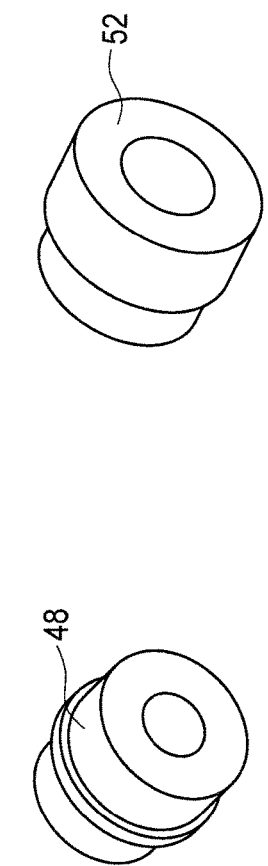
Figure 6B:
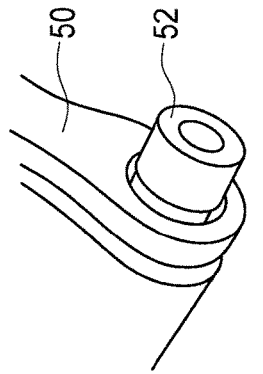
Figure 7B:
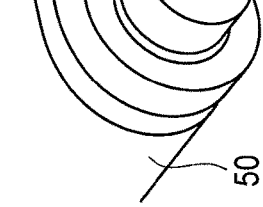
Figure 10:
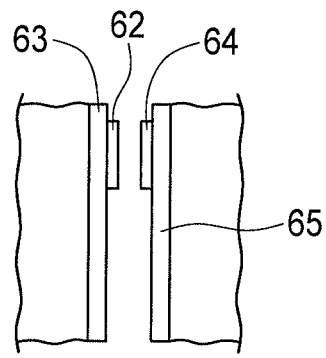
FIG. 10 is a view showing an RFID tag workpiece identifying arrangement.
Figure 11:
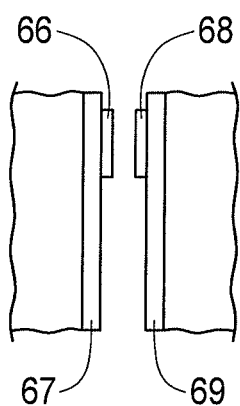
FIG. 11 is a view showing an optical workpiece identifying arrangement.

FIGS. 5A and 5B show an example of an LED workpiece 48 attached to an appliance 50. FIGS. 6A and 6B show a workpiece 52 capable of emitting an ultrasound signal, for example in the range of 2 kHz to 8 MHz, while FIG. 6B shows the ultrasound workpiece 52 attached to an appliance 54. FIGS. 7A and 7B show an iontophoresis tip embodiment; 7A shows the iontophoresis tip 56, while 7B shows the iontophoresis tip in an appliance 58. As indicated above, the above three specific examples discussed above are only a few of the many specific workpiece tips which can be utilized with one appliance.

Each workpiece will typically require a different driving signal, particularly adapted to operate it. When a workpiece is attached to the handle, there must first be a recognition of the particular workpiece. This can be done in a variety of ways. One way is to identify the particular workpiece by its impedance/resistance value at various frequencies and polarities. A table is shown in FIG. 8 which illustrates this approach for the various workpieces set out above. This will require use of the signal generator portion of the signal assembly 34. Each workpiece element will have a particular impedance value which can be recognized. The signal generator 38 will produce a signal that sweeps from a low frequency, approximately 1 kHz to 2 GHz. This frequency range enables the identification of the six workpiece elements specified in FIG. 8. The signal will be applied through the respective interface assemblies to the workpiece element. Each element will have a particular resistance which can be associated in a table in a memory portion of the sensing module 36 or the microprocessor 40. For instance, for an LED, the sensing circuit will identify an open circuit in one direction and less than 0.4 Ohms in the other direction, since it is an LED in a diode configuration. For a thermoelectric element, the resistance/impedance value will be 0-1 Ohm in both directions, while a heating element will be 2-4 Ohms in both directions. An iontophoresis element will have a variable resistance of 10 Ohms to 10K Ohms. An ultrasound transducer will be identified by an open circuit to 20 kHz and then a peak of 50 Ohms or less, somewhere between 20 kHz and 10 MHz. A radio frequency workpiece will be an open circuit to 2 GHz. If there is an open circuit beyond 2 GHz, there is no workpiece installed. Other types of workpieces will have a known impedance/resistance value which can be stored in memory in the appliance.

A wide range of workpiece elements thus can be dynamically identified, but this is not necessary to the invention. For instance, an appliance can be adapted to a non-active head and alternatively a heated head, or an LED head.

FIGS. 5A and 5B show an example of an LED workpiece 48 attached to an appliance 50. FIGS. 6A and 6 B show a workpiece 52 capable of emitting an ultrasound signal, for example in the range of 2 kH$_z$ to 8 MH$_z$, while FIG. 6B shows the ultrasound workpiece 52 attached to an appliance 50. FIGS. 7A and 7B show an iontophoresis tip embodiment; 7A shows the iontophoresis tip 56, while 7B shows the iontophoresis tip in an appliance 50. As indicated above, the above three specific examples discussed above are only a few of the many specific workpiece tips which can be utilized with one appliance.

Once the particular workpiece has been identified, the microprocessor and the signal generator 38 will provide the correct operating signal for the recognized workpiece. With respect to the examples above, the various workpieces and the appropriate electrical signals are identified in the FIG. 9 table. Each workpiece has a particular operating signal. The correct operating signal is stored in the microprocessor 40, and when the workpiece is recognized, the microprocessor will send a control signal to the signal generator 38 to produce the correct operating signal. FIG. 9 sets forth the correct operating signals for a variety of workpieces. Other workpieces will require other operating signals.

Figure 3:
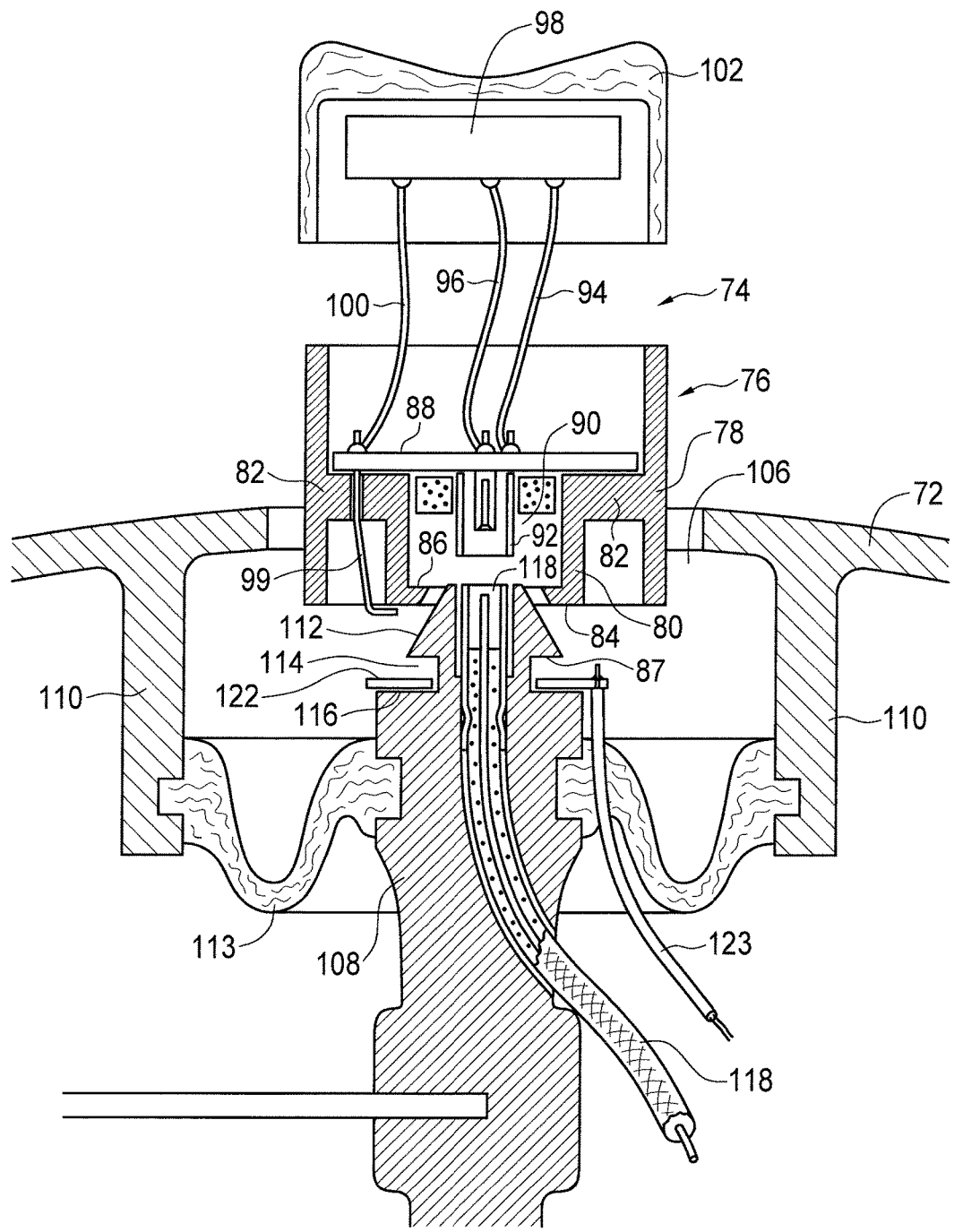
FIG. 3 is a cross-section of a portion of one embodiment of the present invention.
Figure 4:
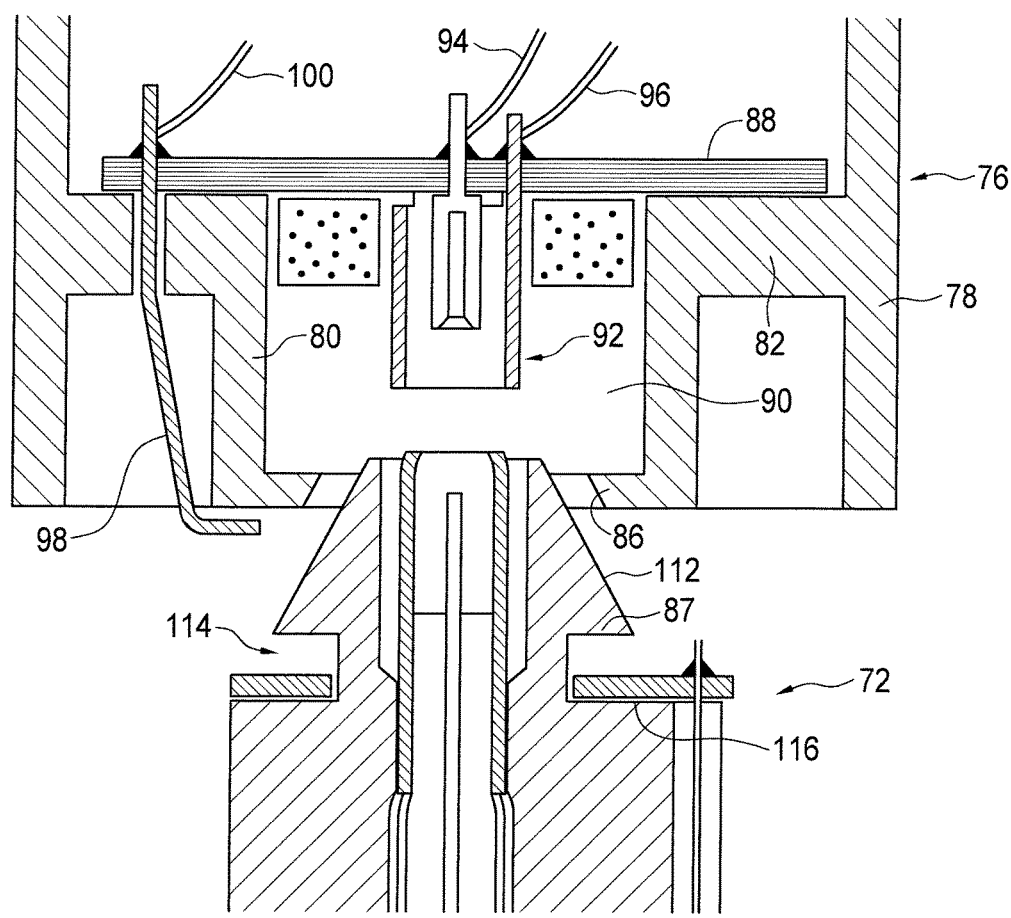
FIG. 4 is a cross-section of a smaller portion of FIG. 3.

FIGS. 3 and 4 show the particular physical arrangement and connection between the workpiece and the body/handle. In each figure, the handle is identified at 72, while the workpiece is identified generally at 74. The workpiece includes a base portion 76, including an outer circular wall 78 and an inner circular wall 80 connected to the outer wall by an intermediate flat portion 82. The lower edge 84 of inner wall 80 includes one inwardly extending portion 86 which snaps on to a corresponding lip 87 in the handle, as explained in more detail below the workpiece includes a flat element 88 which fits on intermediate portion 82, covering the opening 90 defined by the inner wall. Extending downwardly from element 88 is an electrical connector 92. Electrical connector 92 can be in the form of a coaxial connector which has two electrical leads 94 and 96 extending therefrom to the workpiece element 98 which can, as indicated previously, be a variety of elements such as set forth, for example, in Table 9. An additional spring connector 99 is positioned between the inner and outer wall and extends through the intermediate member 82 to the flat plate 88. A lead 100 extends from the flat plate 88 to the workpiece element 98, if a third connector is required. The workpiece includes a cover element 102 which mates with the outer wall 78 of the workpiece base 76 to form a complete workpiece.

The appliance body/handle includes an opening 106 into which the workpiece fits. The handle includes a mounting member 108 which is supported within the handle. Mounting member 108 is also supported to a circular depending assembly 110 with a flexible element 113 connecting the mounting member 108 and depending assembly 110. The mounting member 108 is thus free to move to some extent to accommodate the attachment of the workpiece. At the upper end of the mounting member 108 is a portion 112 which is conical in shape and is configured so that a space 114 exists between portion 112 and an upper surface 116 of the mounting member 108. The conical portion is configured in such a manner that the inwardly extending portion 86 of inner wall 80 of the workpiece can snap under the conical member 112, holding the workpiece in place. Extending through mounting member 108 is an electrical connection 118 which can be a coaxial cable. Coaxial cable 118 mates with the coaxial cable 92 in the workpiece when the workpiece is snapped onto the handle, providing a secure, reliable electrical connection.

Additional spring lead 99 connects electrically to a face connector element 122 on the upper surface of the mounting element located below the conical portion 112. Face connector 122 is electrically conductive. An electrical connection 123 provides a signal form the appliance to the spring connector 99, if needed. Hence, the arrangement shown includes three separate electrical connections where three connections are necessary. In some cases, only two connections may be necessary.

Further with respect to the above specific workpieces, an LED workpiece can, for instance, be driven with a regulated current, in which case the appliance works as a sensing power supply to provide the correct voltage to match the polarity and impedance of the LED workpiece. For an LED only, two electrical connections are required.

A thermoelectric element workpiece can operate from a constant current appliance setting but typically it will be a different current level than that used for the LED. Two electrical connections are required for this workpiece.

A heating element workpiece has the potential of harming the user by burning unless direct thermal feedback is used to prevent overheating. Typically, this requires an additional electrical connection, but it is possible to use a heating element, the resistance of which changes with temperature. In this arrangement, a separate third connection is not required. If a thermocouple is to be used in the workpiece, a third connection is necessary.

An iontophoresis workpiece requires two connections for a constant current supply in the handle.

Both ultrasound and RF workpieces require two connections and an AC signal that senses the frequency of the particular workpiece. This can be accomplished using a resonant circuit; it is thus possible to use a single connector element for an RF workpiece.

Other specific workpieces will require other specific electrical connections.

Accordingly, an appliance has been disclosed having a handle portion with a plurality of detachable workpieces, which are individually adapted to treat spots and irregularities on the skin, typically, but not necessarily, on the facial skin. Other skin areas may be treated Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A skin treatment appliance with changeable workpieces, comprising:
   an appliance body;
   an appliance body interface assembly for receiving a plurality of separate removable workpieces, wherein each workpiece includes a skin treatment element which has a particular impedance for identification of said workpiece;
   a signal generator with electrical connections to the appliance body interface, wherein the signal generator, controlled by a microprocessor, generates signals which are adapted to control and operate the currently attached workpiece, wherein the signal generator in operation generates a sweeping frequency range wherein the signals automatically sweep from 1 Khz to 2 Ghz, the signals being applied to the workpiece to determine by a sensing circuit the particular impedance of the workpiece;
   at least three workpieces, each workpiece adapted to treat a selected spot skin irregularity, wherein each workpiece element has its particular impedance stored in a memory portion of a sensing module, wherein the microprocessor identifies the attached workpiece by its determined impedance and the stored impedance values and wherein each of the workpieces has an interface assembly for mechanically and electrically connecting to the appliance body interface; and
   wherein the signal generator then provides a correct operating signal for the identified workpiece;
   wherein the workpieces include at least one workpiece having an element impedance which changes from one impedance value to a higher impedance value with a change in frequency of the applied signals.

2. The appliance of claim 1, including an RFID tag on the workpiece and an RFID reader in the appliance body.

3. The appliance of claim 1, including a bar code or other optical member on the workpiece an optical reader in the appliance.

4. The appliance of claim 1, wherein the workpieces include at least three of the following: (1) an LED, (2) a thermoelectric element, (3) a heating element, (4) an iontophoresis element, (5) an ultrasound element and (6) an RF element.

5. The appliance of claim 1, wherein the workpiece includes a latching base member which connects with a mating element on the appliance body to securely position the workpiece in the handle.

6. The appliance of claim 1, wherein the interface assembly includes a plurality of electrical connections in the body and the body interface assembly and a mating plurality of electrical connections in the workpiece and the workpiece interface assembly, wherein the electrical connections in the workpiece lead to an active element portion in the workpiece.

7. The appliance of claim 6, wherein the electrical connections include a coaxial connection in the body and a mating coaxial connection in the workpiece.

8. The appliance of claim 7, wherein the workpiece interface includes a spring connector and the body interface includes a mating spring plate, further including an electrical connection between the spring connector in the workpiece and an active portion of the workpiece, and further including an electrical connection from the spring plate in the body to the signal generator.

9. The appliance of claim 1, wherein the interface assembly in the appliance body is flexibly supported to the appliance body.

10. The appliance of claim 1, wherein the appliance body interface includes a central mounting element, wherein the central mounting element is flexibly supported to the appliance body and wherein the central mounting element includes a conical portion which is configured such that an inwardly extending portion of the workpiece can snap under the conical member, holding the workpiece in place and wherein the electrical connection between the body and the workpiece extends through the conical portion into a mating portion of the workpiece.

11. The appliance of claim 1, wherein the workpieces includes at least one workpiece having an element impedance which changes from an open circuit to 50 Ohms or less within a known frequency range of the applied signal.

* * * * *